United States Patent
Ohkubo et al.

(10) Patent No.: US 8,536,394 B2
(45) Date of Patent: Sep. 17, 2013

(54) PROCESS FOR PRODUCING ALKYLATED AROMATIC COMPOUNDS AND PROCESS FOR PRODUCING PHENOLS

(75) Inventors: Tsuneyuki Ohkubo, Ichihara (JP); Shinobu Aoki, Ichihara (JP); Masayasu Ishibashi, Iwakuni (JP); Masao Imai, Yokohama (JP); Terunori Fujita, Yokohama (JP); Kenji Fujiwara, Kamakura (JP)

(73) Assignee: Mitsui Chemicals, Inc., Tokyo (JP)

( * ) Notice: Subject to any disclaimer, the term of this patent is extended or adjusted under 35 U.S.C. 154(b) by 105 days.

(21) Appl. No.: 13/256,626

(22) PCT Filed: Mar. 12, 2010

(86) PCT No.: PCT/JP2010/054172
§ 371 (c)(1),
(2), (4) Date: Sep. 14, 2011

(87) PCT Pub. No.: WO2010/106967
PCT Pub. Date: Sep. 23, 2010

(65) Prior Publication Data
US 2012/0004471 A1    Jan. 5, 2012

(30) Foreign Application Priority Data

Mar. 19, 2009  (JP) ................. 2009-067514

(51) Int. Cl.
*C07C 2/86* (2006.01)
*C07C 37/08* (2006.01)

(52) U.S. Cl.
USPC ........... 585/446; 585/454; 585/457; 585/467; 585/469; 568/798

(58) Field of Classification Search
None
See application file for complete search history.

(56) References Cited

U.S. PATENT DOCUMENTS

| | | | |
|---|---|---|---|
| 4,276,438 A | 6/1981 | Chu | |
| 4,550,218 A * | 10/1985 | Chu | 585/408 |
| 5,015,786 A | 5/1991 | Araki et al. | |
| 5,017,729 A | 5/1991 | Fukuhara et al. | |
| 6,841,704 B2 | 1/2005 | Sakuth et al. | |
| 7,319,177 B2 | 1/2008 | Tsuji et al. | |
| 7,524,788 B2 | 4/2009 | Girotti et al. | |
| 7,790,936 B2 * | 9/2010 | Takai et al. | 568/715 |
| 2004/0111001 A1 | 6/2004 | Dandekar et al. | |
| 2004/0162448 A1 | 8/2004 | Yang et al. | |

FOREIGN PATENT DOCUMENTS

| | | |
|---|---|---|
| GB | 1 504 319 | 3/1978 |
| JP | 50-130693 | 10/1975 |
| JP | 57-091972 | 6/1982 |
| JP | 02-174737 | 7/1990 |
| JP | 2-231442 A | 9/1990 |
| JP | 11-035497 | 2/1999 |
| JP | 2003-523985 | 8/2003 |
| JP | 2004-250430 A | 9/2004 |
| JP | 2005-513116 | 5/2005 |
| WO | WO2008/102664 * | 8/2008 |

OTHER PUBLICATIONS

International Search Report in PCT/JP2010/054172 dated Apr. 20, 2010.
Korean Office Action dated Dec. 28, 2012 issued in connection with Application No. 10-2011-7019432.

* cited by examiner

*Primary Examiner* — Brian J Davis
(74) *Attorney, Agent, or Firm* — Foley & Lardner LLP

(57) ABSTRACT

According to a process of the invention, a ketone, an aromatic compound and hydrogen as starting materials are reacted together in a single reaction step to produce an alkylaromatic compound in high yield. A process for producing phenols in the invention includes a step of performing the above alkylation process and does not increase the number of steps compared to the conventional cumene process. The process for producing alkylated aromatic compounds includes reacting an aromatic compound such as benzene, a ketone such as acetone and hydrogen in the presence of a solid acid substance, preferably a zeolite, and a silver-containing catalyst.

10 Claims, No Drawings

PROCESS FOR PRODUCING ALKYLATED AROMATIC COMPOUNDS AND PROCESS FOR PRODUCING PHENOLS

FIELD OF THE INVENTION

The present invention relates to processes in which an aromatic compound is reacted with a ketone and hydrogen into a corresponding alkylated aromatic compound, and to phenol production processes which include a step of performing the alkylation process. In more detail, the invention relates to processes for producing alkylated aromatic compounds by reacting a ketone, an aromatic compound and hydrogen in a single reaction step using specific catalysts, and to phenol production processes including a step of performing the alkylation process.

BACKGROUND OF THE INVENTION

A reaction between benzene and propylene gives cumene. Oxidation of cumene results in cumene hydroperoxide. The cumene hydroperoxide is acid decomposed into phenol and acetone. A combination of these known reactions is the cumene process which is currently a mainstream process for the production of phenol.

The cumene process gives acetone as a by-product, and is valuable when both phenol and acetone are required. However, if the acetone produced is in excess of demand, the economic efficiency is deteriorated due to the price difference between acetone and starting material propylene. Methods have been then proposed which are aimed at benefiting from the price difference between starting material olefins and by-product ketones. For example, secondary butyl benzene obtained from n-butene and benzene is oxidized and acid decomposed to give phenol and methyl ethyl ketone (Patent Documents 1 and 2). According to this method, the oxidation of the secondary butyl benzene achieves only about 80% selectivity for the target secondary butyl benzene hydroperoxide, with 15% or more by-product acetophenone. This method consequently provides a lower yield of phenol than by the cumene process.

It is also proposed that cyclohexyl benzene obtained from cyclohexene and benzene is oxidized and acid decomposed into phenol and cyclohexanone. Since the cyclohexanone obtained is dehydrogenated into phenol, this method does not technically involve the by-production of ketones. However, the method has a low industrial value because the oxidation of the cyclohexyl benzene provides a low yield of the target cyclohexyl benzene hydroperoxide.

The highest yields in oxidation and acid decomposition are achieved by the cumene process as described above. The problem related to starting material propylene and by-product acetone should be avoided while maintaining the advantageous yields. Methods have been then proposed in which the by-product acetone is treated by various methods and is reused as a material in the cumene process.

Acetone is readily hydrogenated to isopropanol, and the isopropanol is dehydrated to propylene. Patent Document 3 discloses a process in which acetone is reused as a material in the cumene process, in detail cumene is produced by reacting benzene and propylene obtained from acetone as described above. However, the hydrogenation and the dehydration add two steps.

Patent Documents 4 to 6 disclose methods in which isopropanol from the hydrogenation of acetone is directly reacted with benzene to give cumene. In particular, Patent Document 6 discloses a process in which by-product acetone is hydrogenated to isopropanol, the isopropanol is reacted with benzene, and the resultant cumene is reacted to give phenol. In this process, however, the hydrogenation adds a step to the cumene process.

Patent Document 7 describes a method in which by-product acetone is reused without adding a step to the conventional cumene process. In detail, acetone is reacted directly with benzene in the presence of hydrogen using a catalyst system including a solid acid substance and a Cu compound.

RELATED ART

Patent Document 1: JP-A-S57-91972
Patent Document 2: U.S. Patent Application 2004/0162448
Patent Document 3: JP-A-H02-174737
Patent Document 4: JP-A-H02-231442
Patent Document 5: JP-A-H11-35497
Patent Document 6: JP-A-2003-523985
Patent Document 7: JP-A-2005-513116

SUMMARY OF THE INVENTION

The method of Patent Document 7, however, tends to give propane as a by-product during the production of cumene.

It is therefore an object of the present invention to provide an industrial and practical process for producing cumene by directly reacting acetone, benzene and hydrogen. In detail, the invention has an object of providing a novel process for producing alkylated aromatic compounds in which a ketone such as acetone, an aromatic compound such as benzene and hydrogen as starting materials are reacted together in a single reaction step to produce an alkylaromatic compound such as cumene with high yield. It is another object of the invention to provide a process for producing phenols which includes a step of performing the above alkylation process and which does not increase the number of steps compared to the conventional cumene process.

The present inventors studied diligently to achieve the above objects. They have then found that a solid acid substance and a silver-containing catalyst as catalysts can afford an alkylated aromatic compound such as cumene with high yield in a single step of reacting a ketone such as acetone, an aromatic compound such as benzene and hydrogen as starting materials.

A process for producing alkylated aromatic compounds according to the present invention comprises reacting an aromatic compound, a ketone and hydrogen in the presence of a solid acid substance and a silver-containing catalyst.

The aromatic compound is preferably benzene, and the ketone is preferably acetone.

The solid acid substance is preferably a zeolite compound, more preferably a zeolite compound having a ten to sixteen-membered oxygen ring pore, and particularly preferably a zeolite compound having a ten or twelve-membered oxygen ring pore.

The solid acid substance is preferably at least one zeolite compound selected from the group consisting of β-zeolite, mordenite, ZSM-5 zeolite, ZSM-12 zeolite and Y-type zeolite, and is more preferably β-zeolite.

The silver-containing catalyst preferably includes a supported catalyst in which silver is supported on a carrier.

The reaction is preferably catalyzed by a mixture of the solid acid substance and the silver-containing catalyst.

A process for producing phenols according to the present invention comprises:

(a) a step of oxidizing cumene into cumene hydroperoxide;

(b) a step of acid decomposing the cumene hydroperoxide to synthesize phenol and acetone;

(c) a step of reacting the acetone from the step (b) with hydrogen and benzene to synthesize cumene; and (d) a step of circulating the cumene from the step (c) to the step (a);

the step (c) being performed by the process for producing alkylated aromatic compounds described above.

ADVANTAGEOUS EFFECTS OF THE INVENTION

According to the processes for producing alkylated aromatic compounds, a ketone such as acetone, an aromatic compound such as benzene and hydrogen as starting materials are reacted together in a single reaction step to give an alkylaromatic compound such as cumene. The processes of the invention provide industrial and practical advantages. The processes for producing phenols according to the invention include a step of performing the process of producing alkylated aromatic compounds, and the by-product acetone is recycled without increasing the number of steps of the conventional cumene process. The cumene resulting from the production process for alkylated aromatic compounds is identical in quality with cumene obtained from propylene or isopropanol and benzene. The processes of the present invention are thus innovative technology and can produce phenols with process advantages and economic advantages.

PREFERRED EMBODIMENTS FOR CARRYING OUT THE INVENTION

A process for producing alkylated aromatic compounds according to the present invention comprises reacting an aromatic compound, a ketone and hydrogen in the presence of a solid acid substance and a silver-containing catalyst.

The two catalyst components, namely, the solid acid substance and the silver-containing catalyst may be used in any manner without limitation. In an embodiment, the solid acid substance that is an acid catalyst component and the silver-containing catalyst may be physically mixed on a catalyst particle level with a centimeter size. In another embodiment, the catalysts may be finely pulverized and mixed together, and the mixture may be shaped into catalyst particles with a centimeter size. In a still another embodiment, the solid acid substance functioning as an acid catalyst may be used as a carrier, and the silver-containing catalyst may be supported thereon. Alternatively, the solid acid substance may be supported on the silver-containing catalyst as a carrier.

In catalyzing the reaction, the solid acid substance and the silver-containing catalyst are preferably used in the form of a mixture.

The solid acid substances used in the invention are catalysts that function as acids. Examples of the solid acid substances include usual solid acids such as zeolite compounds, silica alumina, alumina, sulfate-promoted zirconia and $WO_3$-promoted zirconia.

In particular, the zeolite compounds that are inorganic crystalline porous compounds mainly composed of silicon and aluminum are suitable alkylation catalysts from the viewpoints of heat resistance and selectivity for the target alkylated aromatic compounds. Suitable zeolite compounds are variable depending on the molecular diameter of the aromatic compounds used as starting materials and the target alkylated aromatic compounds.

For example, a zeolite compound having a ten to sixteen-membered oxygen ring pore is preferably used for the reaction of benzene as the aromatic compound and acetone as the ketone to produce cumene as the alkylated aromatic compound.

Examples of the zeolite compounds having a ten to sixteen-membered oxygen ring pore include ferrierite, heulandite, ZSM-5 zeolite, ZSM-11 zeolite, ZSM-12 zeolite, NU-87 zeolite, theta-1 zeolite, weinbergerite, X-type zeolite, Y-type zeolite, USY-type zeolite, mordenite, dealuminated mordenite, β-zeolite, gmelinite, offretite, cloverite, VPI-5 zeolite and UTD-1 zeolite. Herein, the ten-membered oxygen ring represents the size of pore diameter and indicates that the ring structure forming the pore has a size such that the ring structure contains ten oxygen atoms.

Of the zeolite compounds, those having a pore size approximately the same as the molecular diameter of cumene are preferable, and zeolite compounds having a ten or twelve-membered oxygen ring pore are more preferable. Examples of the zeolite compounds having a ten or twelve-membered oxygen ring pore include Y-type zeolite, USY-type zeolite, mordenite, dealuminated mordenite, β-zeolite, ZSM-12 zeolite and ZSM-5 zeolite. From the viewpoint of cumene selectivity, β-zeolite, mordenite, ZSM-5 zeolite, ZSM-12 zeolite and Y-type zeolite are more preferable, and β-zeolite is particularly preferable.

In the zeolite compounds, the composition ratio between silicon and aluminum (silicon/aluminum) is in the range of 2/1 to 200/1, and in view of activity and heat stability, preferably in the range of 5/1 to 100/1. Further, isomorphously substituted zeolite compounds may be used in which aluminum atoms in the zeolite skeleton are substituted with other metal such as Ga, Ti, Fe, Mn or B.

The shape of the solid acid substances is not particularly limited, and the solid acid substances may be in the form of sphere, cylindrical column, extrudate or crushed particles. The size of the particles of the solid acid substances may be selected in the range of 0.01 mm to 100 mm depending on the size of a reactor.

The solid acid substances may be used singly, or two or more kinds may be used in combination.

The silver (Ag)-containing catalysts (catalyst compositions) used in the invention may contain Ag as the metal element or as a metal compound.

Examples of the metal compounds include silver oxides such as $Ag_2O$; silver halides such as AgCl, AgBr and AgI; and metal cluster compounds such as Pt—Ag and Pd—Ag.

Examples further include silver nitrate, silver lactate, silver acetate, silver benzoate, silver carbonate, silver chromate, silver formate and silver cyanide.

The silver-containing catalysts are not particularly limited as long as they have a capability of hydrogenating the carbonyl functional groups into alcohols. Commercially available hydrogenation catalysts may be used. For example, such catalysts are marketed as supported catalysts on various carriers.

In a preferred embodiment, the silver-containing catalyst includes a supported catalyst in which silver is supported on a carrier (an Ag-supported catalyst).

Examples of the carriers include silica, alumina, silica alumina, titania, magnesia, silica magnesia, zirconia, carbon, acid clay and diatomaceous earth. In a preferred embodiment, at least one carrier is selected from silica, alumina, silica alumina, titania, magnesia, silica magnesia, zirconia and carbon.

The silver-containing catalysts may be used singly, or two or more kinds may be used in combination.

The shape of the silver-containing catalysts is not particularly limited, and the silver-containing catalysts may be in the form of sphere, cylindrical column, extrudate or crushed particles. The size of the particles of the silver-containing catalysts may be selected in the range of 0.01 mm to 100 mm depending on the size of a reactor.

The silver-containing catalyst may be supported on the solid acid substance. Such supported catalysts may be prepared by soaking the solid acid substance in an aqueous silver nitrate solution and calcining the solid acid substance. Alternatively, silver may be bonded with an organic molecule ligand to become soluble in organic solvents, and the solid acid substance may be soaked in a solution of the silver-ligand complex in an organic solvent and thereafter calcined. Taking advantage of the characteristic that some of the complexes are vaporized under vacuum, such complexes may be supported on the solid acid substance by deposition or the like. Further, a coprecipitation method may be adopted in which the solid acid substance is obtained from a corresponding metal salt in the presence of a silver salt which will form a hydrogenation catalyst and thereby the carrier synthesis and the supporting of the metal-containing catalyst are carried out simultaneously.

Examples of the aromatic compounds in the invention include C6-20 compounds such as benzene homologues such as benzene, toluene and xylene, substituted derivatives thereof, naphthalene homologues such as naphthalene and methylnaphthalene, and substituted derivatives thereof. Examples of the ketones include C3-20 compounds. Symmetric or asymmetric ketones may be used. The groups bonded to the carbonyl group may be alkyl groups or aryl groups, namely, the ketones include acetone, methyl ethyl ketone and acetophenone.

In particular, the most important reaction in the industry is the production of cumene from benzene as the aromatic compound and acetone as the ketone. In this case, the molar ratio of benzene to acetone (benzene/acetone) is preferably in the range of 1 to 20. If the molar ratio is below this range, the reaction tends to yield large amounts of diisopropylbenzene and triisopropylbenzene. Diisopropylbenzene and triisopropylbenzene can be converted to cumene by trans-alkylation with benzene in the cumene process. However, the trans-alkylation involves high reaction temperature and thus excessively large amounts of diisopropylbenzene and triisopropylbenzene increase the steam costs and may cause economic disadvantages. If the molar ratio is in excess of the above range, the excess benzene that is collected in a later stage after the reaction puts a heavy load on a distillation column and may cause economic disadvantages.

In the invention, the aromatic compound and the ketone are reacted in the presence of hydrogen. The hydrogen herein may be a molecular hydrogen gas or hydrogen from a hydrocarbon such as cyclohexane that generates hydrogen when subjected to reaction conditions. In the reaction of acetone, benzene and hydrogen, the hydrogen may be theoretically used at least in an equimolar amount relative to the acetone. From the viewpoints of separation and recovery, the hydrogen may be preferably used in an equimolar to fifty-fold molar amount, and more preferably in an equimolar to thirty-fold molar amount relative to the acetone. When the acetone conversion is desired to be less than 100%, the hydrogen amount may be controlled less than the equimolar amount relative to the acetone. In the reaction of the invention, the hydrogen reacts with the oxygen atom in the acetone to form water, and the water produced may be recovered from a reactor outlet together with cumene. An excess of hydrogen over the acetone is not substantially consumed as long as undesirable side reactions take place.

The hydrogen gas is generally supplied to the reaction system continuously, but the supply methods are not particularly limited thereto. In an embodiment, the hydrogen gas may be supplied intermittently such that the hydrogen is supplied at the initiation of the reaction and the supply is suspended during the reaction and restarted after a prescribed time. In the case of a liquid-phase reaction, the hydrogen gas may be supplied while being dissolved in a solvent. In a recycle process, hydrogen gas recovered from the column top together with low-boiling fractions may be resupplied. The pressure of the hydrogen supplied is generally equal to the pressure in the reactor, but may be appropriately adjusted depending on the hydrogen supply methods.

The reaction may be carried out by any methods under any conditions without limitation. Exemplary conditions and methods are described below.

The contact between the starting materials, for example acetone, benzene and hydrogen gas, may take place in a gas-liquid countercurrent flow or a gas-liquid co-current flow. The liquid and gas directions may be descending liquid/ascending gas, ascending liquid/descending gas, ascending liquid/ascending gas, or descending liquid/descending gas.

The reaction temperature in the invention is not particularly limited, but is preferably in the range of 50 to 300° C., and more preferably 60 to 200° C. The reaction pressure is preferably in the range of 0.1 to 500 atm, and more preferably 0.5 to 100 atm.

The amount of the catalysts (the total amount of the solid acid substance and the silver-containing catalyst) is not particularly limited. In an embodiment in which the reaction is performed in a fixed bed flow apparatus, the catalyst amount may be such that the supply amount (weight) of the starting materials (ketone+aromatic compound) per hour divided by the catalyst weight (total weight of the solid acid substance and the silver-containing catalyst), namely, the weight hourly space velocity (WHSV) is preferably in the range of 0.01 to 100/h, and more preferably 0.05 to 50/h.

The weight ratio of the solid acid substance and the silver-containing catalyst is not particularly limited, but the solid acid substance:silver-containing catalyst (weight ratio) is usually in the range of 1:0.01 to 1:100, and preferably 1:0.05 to 1:50. An excessively small weight ratio of the solid acid substance results in insufficient alkylation reaction and low yield of alkylated aromatic compounds such as cumene, often causing economic disadvantages. An excessively large weight ratio of the solid acid substance can be uneconomical because the acetone conversion is lowered.

In the process for producing alkylated aromatic compounds according to the invention, it is considered that the silver-containing catalyst catalyzes hydrogenation of the ketone into alcohol and the solid acid substance catalyzes alkylation between the alcohol and the aromatic compound to an alkylated aromatic compound. That is, the hydrogenation and the alkylation probably take place stepwise in the process of the invention.

In the case where the reaction is performed in a fixed bed reactor, the packing mode of the solid acid substance and the silver-containing catalyst may greatly affect the reaction results. As described hereinabove, the hydrogenation reaction and the alkylation reaction probably take place stepwise in the invention. Accordingly, the catalysts are preferably packed in the appropriate order suited for the reactions in order to catalyze the reactions effectively and prevent undesired side-reactions.

In particular, increasing the hydrogen pressure or the reaction temperature to accelerate the reaction rate usually involves undesired side-reactions that are not observed at low hydrogen pressure or low reaction temperature. In such cases, the reaction results can be greatly influenced by the catalyst packing manner.

For example, the catalysts may be packed in the appropriate order suited for the reactions in a manner such that: (1) the solid acid substance and the silver-containing catalyst are mixed homogeneously and packed in the reactor; (2) a catalyst layer is formed in which the concentration of the silver-containing catalyst is decreased at a constant rate from the upstream side to the downstream side of the catalyst layer while the concentration of the solid acid substance is increased at a constant rate from the upstream side to the downstream side; (3) the solid acid substance supporting the silver-containing catalyst is packed; (4) the silver-containing catalyst forms a layer (on the upstream side), and the solid acid substance and the silver-containing catalyst together form a layer (on the downstream side); (5) the silver-containing catalyst forms a layer (on the upstream side) and the solid acid substance supporting the silver-containing catalyst forms a layer (on the downstream side); (6) the solid acid substance and the silver-containing catalyst form a layer (on the upstream side) and the solid acid substance forms a layer (on the downstream side); or (7) the solid acid substance supporting the silver-containing catalyst forms a layer (on the upstream side) and the solid acid substance forms a layer (on the downstream side). Here, the term upstream side means an inlet side of the reactor, in other words, this term indicates that the starting materials are passed through the layer in the first half of the reaction. The term downstream side means an outlet side of the reactor, in other words, this term indicates that the materials are passed through the layer in the last half of the reaction.

In an embodiment for carrying out the invention, the reaction may be carried out in a diluted reaction system by supplying a solvent or a gas that is inert to the catalysts and the reaction materials.

The reaction may be performed by a batch process, a semi-batch process or a continuous flow process. The reaction phase may be a liquid phase, a gas phase or a gas-liquid mixed phase. The catalyst packing modes include fixed bed systems, fluidized bed systems, suspended bed systems and multistage fixed bed systems.

In the invention, the solid acid substance and the silver-containing catalyst are preferably dehydrated by known methods. In the case of fixed bed reaction system, the solid acid substance and the metal-containing catalyst may be dehydrated by being held at a temperature of 300° C. or above for at least 10 minutes while passing an inert gas such as nitrogen or helium through the reactor packed with the catalysts. To develop the activity of the silver-containing catalyst that is a hydrogenation catalyst, the dehydration treatment may be followed by a treatment under a stream of hydrogen.

In the event that the catalyst activity is lowered after a time of reaction, the solid acid substance and the silver-containing catalyst may be regenerated by known methods to recover the activity.

To maintain the yield of the alkylated aromatic compounds such as cumene, two or three reactors may be arranged in parallel to adopt a merry-go-round system in which the catalysts in one reactor are regenerated while the reaction is continuously carried out in the remaining one or two reactors. When the process involves three reactors, two of these reactors may be connected in series to stabilize the production output. When the reaction is carried out in a fluidized bed flow reaction system or in a moving bed reaction system, part or the whole of the catalysts may be withdrawn from the reactor continuously or intermittently while a corresponding amount of the catalysts is newly added to maintain the activity at a constant level.

By the processes for producing alkylated aromatic compounds described hereinabove, cumene may be obtained directly from, for example, acetone that is by-produced in the production of phenols.

The cumene obtained by the process of the invention may be used as a material for the production of phenol and acetone. In detail, the process of the invention may be used in a phenol production process in which cumene is oxidized and decomposed through the following steps (a) to (d). Various modifications may be made to such processes. The step (c) is performed according to the process for producing alkylated aromatic compounds as described hereinabove.

Step (a): Cumene is oxidized into cumene hydroperoxide.
Step (b): The cumene hydroperoxide is acid decomposed to give phenol and acetone.
Step (c): The acetone from the step (b) is reacted with hydrogen and benzene to give cumene.
Step (d): The cumene from the step (c) is circulated to the step (a).

In more detail, the process for producing phenols according to the invention comprises:
(a) a step of oxidizing cumene into cumene hydroperoxide;
(b) a step of acid decomposing the cumene hydroperoxide to synthesize phenol and acetone;
(c) a step of reacting the acetone from the step (b) with hydrogen and benzene to synthesize cumene; and
(d) a step of circulating the cumene from the step (c) to the step (a).

The step (c) is performed by the process for producing alkylated aromatic compounds described above. In detail, in the step (c), the aromatic compound and the ketone are reacted with hydrogen in the presence of the solid acid substance and the silver-containing catalyst.

According to the step (c), the by-product acetone can be converted to cumene in a single reaction step. The cumene obtained may be used as a material for the production of phenols.

In the phenol production process, the step (a) may be performed by a conventional method without limitation as long as cumene hydroperoxide is obtained. The step (b) may be carried out by a known method without limitation as long as phenol and acetone are obtained. The cumene initially fed in the step (a) may be obtained by a known method or by the process for producing alkylated aromatic compounds according to the invention.

EXAMPLES

The present invention will be described in greater detail by presenting examples without limiting the scope of the invention.

Example 1

Preparation of Catalyst

A 300 ml pear shaped flask was charged with 30.0 g of silica gel powder (CARIACT Q-15, manufactured by Fuji Silysia Chemical Ltd.) and a solution of 6.4 g of silver lactate 0.5 hydrate (Wako Pure Chemical Industries, Ltd.) in 100 ml of ion exchange water. Water was distilled away at a reduced pressure of 10 mm Hg at 40 to 50° C., and the residue was dried overnight under a stream of nitrogen. Subsequently, reduction treatment was performed in a hydrogen atmosphere while increasing the temperature from 100° C. to 320° C. in 5 hours, followed by natural cooling. As a result, 32.9 g of 10% Ag/silica gel catalyst (supported catalyst) was obtained as black powder.

[Production of Cumene]

A fixed bed reaction apparatus was used which was equipped with a high-pressure feed pump, a high-pressure hydrogen mass flow controller, a high-pressure nitrogen mass flow controller, an electric furnace, a reactor having a catalyst-packing part, and a back pressure valve. A pressurized liquid-phase downflow reaction was carried out in the reaction apparatus.

The reactor was a SUS 316 reactor having an inner diameter of 1 cm. The 10% Ag/silica gel catalyst was compacted at 20 MPa and was classified to 250 to 500 μm. The silver-containing catalyst in an amount of 6.0 g was mixed with 1.0 g of β-zeolite (manufactured by JGC Catalysts and Chemicals Ltd., compacted at 20 MPa and classified to 250 to 500 μm), and the mixture was packed in the reactor to form a catalyst layer.

The pressure was increased to 4.5 MPa with hydrogen. Under a stream of hydrogen at 8.3 ml/min, a benzene/acetone (5/1 molar ratio) mixture liquid was passed at 175° C. at a rate of 0.50 g/h (WHSV=0.07/h, hydrogen/acetone molar ratio=20).

The reaction products were sampled at the outlet of the reactor. The gas phase and the liquid phase were analyzed by gas chromatography.

The reaction results are set forth in Table 1. The cumene selectivity is high compared to the result in Comparative Example 1 below.

Comparative Example 1

Reaction was performed in the same manner as in Example 1, except that the 10% Ag/silica gel catalyst was replaced by 1.0 g of copper chromite (G99b manufactured by Sud-Chemie AG, element mass %: Cu 35%, Cr 31%, Ba 2%, Mn 3%). The reaction results are set forth in Table 1. A large amount of propane was produced as a by-product.

[Table 1]

step to yield a corresponding alkylated aromatic compound. The processes of the invention thus provide industrial and practical advantages. By the processes of the invention, cumene can be obtained directly from acetone that is by-produced in the production of phenols by the cumene process. The cumene obtained according to the invention may be used as a material for the production of phenol and acetone. The present invention may be applied to processes in which cumene is oxidized and then decomposed.

The invention claimed is:

1. A process for producing alkylated aromatic compounds, comprising reacting an aromatic compound, a ketone and hydrogen in the presence of a solid acid substance and a silver-containing catalyst.

2. The process for producing alkylated aromatic compounds according to claim 1, wherein the aromatic compound is benzene, and the ketone is acetone.

3. The process for producing alkylated aromatic compounds according to claim 1, wherein the solid acid substance is a zeolite compound.

4. The process for producing alkylated aromatic compounds according to claim 1, wherein the solid acid substance is a zeolite compound having a ten to sixteen-membered oxygen ring pore.

5. The process for producing alkylated aromatic compounds according to claim 1, wherein the solid acid substance is a zeolite compound having a ten or twelve-membered oxygen ring pore.

6. The process for producing alkylated aromatic compounds according to claim 1, wherein the solid acid substance is at least one zeolite compound selected from the group consisting of β-zeolite, mordenite, ZSM-5 zeolite, ZSM-12 zeolite and Y-type zeolite.

7. The process for producing alkylated aromatic compounds according to claim 1, wherein the solid acid substance is β-zeolite.

8. The process for producing alkylated aromatic compounds according to claim 1, wherein the catalyst is a supported catalyst in which silver is supported on a carrier.

9. The process for producing alkylated aromatic compounds according to claim 1, wherein the reaction is catalyzed by a mixture of the solid acid substance and the silver-containing catalyst.

10. A process for producing phenols, comprising:
(a) a step of oxidizing cumene into cumene hydroperoxide;
(b) a step of acid decomposing the cumene hydroperoxide to synthesize phenol and acetone;
(c) a step of reacting the acetone from the step (b) with hydrogen and benzene to synthesize cumene; and
(d) a step of circulating the cumene from the step (c) to the step (a);

TABLE 1

| | | | | Selectivity (%)/acetone | | | | |
|---|---|---|---|---|---|---|---|---|
| | Reaction temperature | Hydrogen/acetone (molar ratio) | Acetone conversion (%) | Propane | Cumene | Diisopropyl benzene | Triisopropyl benzene | High-boiling fractions |
| Ex. 1 | 175° C. | 20 | 99.9 | 3.5 | 77.2 | 16.1 | 0.3 | 2.9 |
| Comp. Ex. 1 | 175° C. | 20 | 99.9 | 39.3 | 50.2 | 7.8 | 0.2 | 2.5 |

INDUSTRIAL APPLICABILITY

According to the present invention, a ketone and an aromatic compound may be reacted directly in a single reaction the step (c) being performed by the process for producing alkylated aromatic compounds according to claim 1.

* * * * *